US006936187B2

(12) United States Patent
Lynch et al.

(10) Patent No.: US 6,936,187 B2
(45) Date of Patent: Aug. 30, 2005

(54) FUNCTIONALIZED CUBIC LIQUID CRYSTALLINE PHASE MATERIALS AND METHODS FOR THEIR PREPARATION AND USE

(76) Inventors: Matthew Lawrence Lynch, 3769 Harvard Acres, Mariemont, OH (US) 45227; Patrick Thomas Spicer, 442 Hillcrest Dr., Wyoming, OH (US) 45215

(*) Notice: Subject to any disclaimer, the term of this patent is extended or adjusted under 35 U.S.C. 154(b) by 30 days.

(21) Appl. No.: 10/075,551

(22) Filed: Feb. 14, 2002

(65) Prior Publication Data

US 2002/0153509 A1 Oct. 24, 2002

Related U.S. Application Data

(60) Provisional application No. 60/270,307, filed on Feb. 21, 2001.

(51) Int. Cl.[7] .............................................. C09K 19/52
(52) U.S. Cl. ................... 252/299.01; 514/937; 514/964
(58) Field of Search ............................. 427/2.22, 2.21, 427/2.19, 2.16, 213.33, 2.14, 212, 213.3, 213.34, 213.35, 213.36, 222; 424/421, 439, 456, 450, 400, 409, 417, 418, 419, 420; 349/10; 252/299.01; 514/937, 964

(56) References Cited

U.S. PATENT DOCUMENTS

| | | | |
|---|---|---|---|
| 4,557,935 A | | 12/1985 | Ekenstam et al. |
| 5,196,201 A | * | 3/1993 | Larsson et al. ............. 424/422 |
| 5,230,895 A | | 7/1993 | Czarnecki et al. |
| 5,371,109 A | * | 12/1994 | Engstrom et al. ........... 514/786 |
| 5,531,925 A | | 7/1996 | Landh et al. |
| 5,593,663 A | | 1/1997 | Leng et al. |
| 5,753,259 A | | 5/1998 | Engstrom et al. |
| 5,756,108 A | | 5/1998 | Ribier et al. |
| 5,807,573 A | | 9/1998 | Ljusberg-Wahren et al. |
| 6,228,383 B1 | * | 5/2001 | Hansen et al. ............. 424/407 |
| 6,274,574 B1 | * | 8/2001 | Akashe et al. ............. 514/182 |
| 6,482,517 B1 | * | 11/2002 | Anderson .............. 428/402.24 |
| 6,506,391 B1 | * | 1/2003 | Biatry ....................... 424/401 |
| 6,656,385 B2 | * | 12/2003 | Lynch et al. ........... 252/299.61 |
| 6,773,627 B2 | * | 8/2004 | Lynch et al. ........... 252/299.01 |

FOREIGN PATENT DOCUMENTS

| | | | | |
|---|---|---|---|---|
| EP | 0 429 419 | * | 5/1991 | ......... A61L/27/00 |
| WO | WO 98/47487 A1 | | 10/1998 | |
| WO | WO 99/12640 A1 | | 3/1999 | |
| WO | WO 01/68139 A1 | | 9/2001 | |

OTHER PUBLICATIONS

K. Fontell, "Cubic Phases in Surfactant and Surfactant-like Lipid Systems", Colloid Polymer Science 268:264–285 (1990).*

S. Engstrom, "A Study of Polar Lipid Drug Carrier Systems Undergoing a Thermoreversible Lamellar-to-Cubic Phase Transition", International Journal of Pharmaceuticals, 86:137–145 (1992).*

S. Engstrom, "Phase Behaviour of the Lidocaine–Monoolein–Water System", International Journal of Pharmaceuticals, 79:113–122 (1992).*

(Continued)

*Primary Examiner*—Mark F. Huff
*Assistant Examiner*—Jennifer R. Sadula
(74) *Attorney, Agent, or Firm*—Frost Brown Todd LLC (57) ABSTRACT

Functionalized cubic gel precursors, functionalized cubic liquid crystalline gels, dispersions of functionalized cubic gel particles and functionalized cubic gel particles are disclosed. Methods for preparing and using the precursors, gels, dispersions, and particles are also disclosed. The precursors, gels, dispersions, and particles are used to deliver active ingredients to substrates.

60 Claims, 2 Drawing Sheets

OTHER PUBLICATIONS

K. Alfons, "Drug Compatibility with the Sponge Phases Formed in Monoolein, Water and Propylene Glycol or Poly(ethylene glycol)", Journal of Pharmaceutical Sciences, 87(12):1527–1530 (1998).*

R. G. Laughlin, Equilibrium vesicles: fact or fiction?, Colloids and Surfaces A: Physicochemical and Engineering Aspects 128 (1997) 27–38.

J. C. Shah, *Cubic phase gels as drug delivery systems*, Advanced Drug Delivery Reviews 47 (2001) 229–250.

N. Cruise, Letter to the Editor "Mesoporous Alumina Made from a Bicontinuous Liquid Crystalline Phase," Journal of Colloid and Interface Science 241, 527–529 (2001).

E. M. Landau, *Lipidic cubic phases: A novel concept for the crystallization of membrane proteins*, Proc. Natl. Acad. Sci. USA vol. 93, pp. 14532–14535, Dec. 1996.

H. Qiu, *The phase diagram of the monoolein/water system: metastability and equilibrium aspects*, Biomaterials 21 (2000) 223–234.

M. L. Lynch, *Aqueous–Phase Behavior and Cubic Phase–Containing Emulsions in the $C_{12}E_2$—Water System*, Langmuir 2000, 16, 3537–3542.

R. G. Laughlin, *An Expedient Technique for Determining Solubility Phase Boundaries in Surfactant–Water Systems*, Journal of Collid and Interface Science, vol. 55, No. 1, pp. 239–241, Apr. 1976.

V. Luzzati, *Structure of the Cubic Phases of Lipid–Water Systems*, Nature, vol. 220, pp. 485–488, Nov. 2, 1968.

J. R. Bellare, *Controlled Environment Vitrification System: An Improved Sample Preparation Technique*, Journal of Electron Microscopy Technique, 10:87–111 (1988).

M. R. Porter, *Handbook of Surfactants*, $2^{nd}$ ed., Blackie Academic & Professional, 1994, pp. 188–236.

V. Luzzati, *Cubic Phases of lipid–containing systems*, Journal Mol. Biol., 1993, 229, 540–551.

H. G. Schnering, *Nodal surfaces of fourier series: fundamental invariants of structured matter*, Condensed Matter 83, 407–412 (1991).

G. Rummel, *Lipidic Cubic Phases: New matrices for the three–dimensional crystallization of membrane proteins*, Journal of Structural Biology 121, 92–91 (1998).

H. Ljusberg–Wahren, *Dispersion of the cubic liquid crystalline phase–structure, preparation and functionality aspects*, Chimica Oggi, 1996, 14, 40–43.

Norling, *Formulation of a drug delivery system based on a mixture of monoglycerides and triglycerides for use in the treatment of periodontal disease*, Journal Clin. Periodontal, 1992, 19 (9, Pt.2) 687–692.

K. Lindell, *Influence of a charged phospholipid on the release pattern of timolol maleate from cubic liquid crystalline phases*, Progr Colloid Polym Sci (1998) 108:111–118.

S. Engstrom, *Cubic phases for studies of drug partition into lipid bilayers*, European Journal of Pharmaceutical Sciences 8 (1990, 243–254.

R. G. Laughlin, *The aqueous phase behavior of surfactants*, Academic Press, NY, 1994, pp. 255.

J. S. Kim, et al., *Drug Formulations that Form a Dispersed Cubic Phase when mixed with Water*, Proceed. Int'l. Symp. Control. Rel. Bioact. Mater., 27 (2000) Controlled Release Society, Inc., pp. 1118 & 1119.

* cited by examiner

FUNCTIONALIZED CUBIC LIQUID CRYSTALLINE PHASE MATERIALS AND METHODS FOR THEIR PREPARATION AND USE

This application claims the benefit of provisional application Ser. No. 60/270,307, filed Feb. 21, 2001.

FIELD OF THE INVENTION

This invention relates to functionalized cubic liquid crystalline phases and methods for their preparation and use. More specifically, this invention relates to functionalized cubic liquid crystalline phase materials that have properties tailored to specific uses.

BACKGROUND OF THE INVENTION

Much of the interest in bicontinuous cubic phase liquid crystals is a consequence of their unique structure. They are composed of mixtures of lipid and water arranged into bilayers. The bilayers, in turn, are twisted into a periodic, three-dimensional structure that minimizes the energy associated with bending the bilayers (i.e., minimize curvature energy). See Hyde, S., Andersson, S., Larrson, K., Blum, Z., Landh, T., Lidin, S., Ninham, B. W., *The Language of Shape*, Elsevier Press, New York, 1997. These structures are 'honeycombed' with bicontinuous domains of water and lipid reminiscent of an organic zeolite or highly structured micro emulsion. As such the structure can simultaneously accommodate water-soluble, lipid-soluble, and amphiphilic molecules, and provide pathways for diffusion of water-soluble, and lipid-soluble, materials. While there have been a number of proposed cubic phases, there are three common bicontinuous liquid crystals structures: $P_{n3m}$ (D-surface), $I_{a3d}$ (G-surface), and $I_{m3m}$ (P-surface). See Luzzati, V., Vargas, R., Mariani, P., Gulik, A., Delacroix, H., *J. Mol. Biol.*, 1993, 229, 540–551. These structures can be difficult to express in rigorous mathematical terms. However, if expressed in terms of nodal surfaces, structure and shape can be approximated. See von Schnering, H. G., Nesper, R. Z., *Phys. B-Condensed Matter*, 1991, 83, 407–412. The phase behavior of a broad range of monoglycerides has been documented, particularly for monoolein. See Qiu, H., Caffrey, M., *Biomaterials*, 1999, 21(3), 223–234. Monoolein-based bicontinuous cubic liquid crystal phase have good temperature stability, high internal surface area, gel-like viscosity, relative insensitivity to salt and solvent compositions, and use low cost raw materials which make them practical for commercial applications. Monoolein naturally exhibits $P_{n3m}$ and $I_{a3d}$ structure, with $I_{m3m}$ structure present with the addition of proteins. See Rummel, G., Hardmeyer, A., Widmer, C., Chiu, M. L., Nollert, P., Locher, K. P., Pedruzzi, I., Landau, E. M., Rosenbusch, J. P., *J. Structural Biology*, 1998, 121, 82–91.

Cubic phase liquid crystals have been used in gel, dispersion and precursor form. 'Gels' are mixtures that contain a majority of the cubic phase liquid crystal. It is common for mixtures to exclusively contain cubic liquid crystal phase. Applications for these gels can range from drug delivery vehicles (See Shah, J. C., Sadhale, Y., Chilukuri, D. M., *Adv. Drug Delivery Rev.*, 2001, 47(2–3), 229–250), to a matrix in which membrane proteins can be crystallized (See Landau, E., Rosenbusch, J., *Proc. Natl. Acad. Sci. U.S.A.*, 1996, 93(25), 14532–14535), or in which mesoporous nanoparticles can be formed (See Cruise, N., Jansson, K., Holmberg, K., *J. Colloid Interface Sci.*, 2001, 241(2), 527–529).

Nielsen, WO 98/47487, discloses compositions of bioadhesive liquid crystal gels, including the cubic phase liquid crystals and precursors. Compositions include an active, a cubic phase forming lipid, and a structurant that is added without changing the structure of the liquid crystal. The structurant, as disclosed, imparts no properties to the composition other than a diluent. Further, no reference is made regarding the use of tethers as structurants.

Engstrom et al., U.S. Pat. No. 5,753,259, discloses a composition and method of use of liquid crystal gels, including cubic phase liquid crystals, for controlled release applications. The disclosed gels are fabricated from a mixture of lipid, solvent, and bioactive materials including nucleic acids. While the use of monoolein and phospholipid is disclosed, the express function is limited. For example, the disclosure does not disclose the ability to change compositional properties by the application of a stimulus, such as a change in pH.

'Dispersions' are particles of cubic liquid crystalline phase material that are often submicron in size. Particles are generally dispersed in a liquid medium and are often termed Cubosomes. High-pressure homogenization of a mixture of lipid and liquid generally makes colloidally unstable dispersions of cubic phase liquid crystals. This requires high pressures and numerous passes before homogeneous nanoparticle dispersions are produced (See Ljusberg-Wahren, H., Nyberg, L., Larsson, K., *Chimica Oggi*, 1996, 14, 40–43). Cubosomes have distinct practical advantages over vesicles and liposomes because cubosomes are an equilibrium phase (See Laughlin, R. G. *Colloids and Surfaces A*, 1997, 128, 27–38). Cubosomes also possess much greater internal surface area than vesicles or liposomes and are more resilient against degradation.

Anderson, WO 99/12640, and Landh et al., U.S. Pat. No. 5,531,925, disclose cubic phase compositions and preparations for delivery and uptake of active agents. The particles comprise a center containing liquid crystalline material. However, the particles disclosed in Anderson are coated with an exterior of solid particles. Further, the particles disclosed in Landh are coated with another liquid crystalline material.

'Precursors' are mixtures that are not cubic phase liquid crystals but form cubic phase liquid crystals as a consequence of a stimulus. Precursors can be used to dispense a mixture in a form that readily flows, but spontaneously converts to a more viscous liquid crystal gel or a more flowable dispersion with the stimulus at a target location. This is applicable to treatments for periodontal disease (See Norling, Tomas, Lading, Pia, Engstroem, Sven, Larsson, Kare, Krog, Niels, Nissen, Soeren Soe, *J. Clin. Periodontol*, 1992, 19(9, Pt. 2), 687–92.

Larsson et al., U.S. Pat. No. 5,196,201, discloses the preparation and composition of precursors used as implants to treat ailments such as the repair of bone tissue. These precursors are composed of a water-based liquid, lipid, and optionally a triglyceride mixed to form a more concentrated L2 or D phase, which flows more readily, and converts to cubic phase upon the addition of water. Leng et al., U.S. Pat. No. 5,593,663, discloses combinations and preparations of antiperspirant, which uptake sweat upon application to form a viscous liquid crystalline phase, including cubic phase. However, neither of these materials contains functionalization materials.

Cubic liquid crystalline phase materials are limited in use due to restriction of their natural, or unmodified, properties. For example, the natural properties of cubic phases limit the ability to solubilize active ingredients. In fact, broad classes of actives do not effectively load (or subsequently release)

because the cubic phase lacks specific interaction with the loaded active. If the active is modified to effectively load in the cubic phase, it may lose its effectiveness. It has been suggested that the inclusion of zwitterionic phospholipids may cause increase in the absorption of active. Even if true, however, the results would be difficult to prove. (See Engstro, Sven, Norde, Tomas Petersson, Nyquist, Hakan, *Eur. J. Pharm. Sci.* 1999, 8(4), 243–254). It has also been suggested that the release of timolol maleate from a cubic phase liquid crystal could be affected by the inclusion of phospholipid in the cubic phase. However, the resulting concentrations of surfactant are insufficient to provide any practical value for many applications. (See Lindell, K., Engblom, J., Jonstromer, M., Carlsson, A., Engstrom, S., *Progr. Colloid Polym. Sci*, 1998, 108:111–118). Neither reference discloses the modification of cubic phase liquid crystal dispersions or precursors.

Further, there are no commercially convenient ways to provide specific targeting or enhanced deposition of actives from cubic phase. Finally, there are no cubic phases suitable for 'on demand' applications. "On demand' refers to changes in the properties of cubic phase as a consequence of some stimulus, such as change in pH. As a result, a technique is needed to modify the cubic phase and significantly increase the utility of cubic phase.

SUMMARY OF THE INVENTION

A cubic liquid crystalline phase precursor comprising an amphiphile (A) capable of forming a cubic liquid crystalline phase, an optional solvent (B), and an additive (C) selected from the group consisting of an anchor, a tether, and combinations thereof, and wherein (A), (B), and (C) are present in mass fractions relative to each other such that 1.0=a+b+c, wherein a is the mass fraction of (A), b is the mass fraction of (B), and c is the mass fraction of (C), and wherein 1.0>a>0, 1.0>b>0, 1.0>c>0; with the proviso that a, b, and c do not fall within a cubic liquid crystalline phase region on a phase diagram representing phase behavior of (A), (B), and (C).

A bulk cubic liquid crystalline gel comprising an amphiphile (A) capable of forming a cubic liquid crystalline phase, a solvent (B), and an additive (C) selected from the group consisting of an anchor, a tether, and combinations thereof, and wherein (A), (B), and (C) are present in mass fractions relative to each other such that 1.0=a+b+c, wherein a is the mass fraction of (A), b is the mass fraction of (B), and c is the mass fraction of (C), and wherein 1.0>a>0, 1.0>b>0, 1.0>c>0; and with the proviso that a, b, and c fall within a cubic liquid crystalline phase region on a phase diagram representing phase behavior of (A), (B), and (C).

A dispersion of cubic liquid crystalline gel particles comprising an amphiphile (A) capable of forming a cubic liquid crystalline phase, a solvent (B), and an additive (C) selected from the group consisting of an anchor, a tether, and combinations thereof, wherein (A), (B), and (C) are present in mass fractions relative to each other such that 1.0=a+b+c, wherein a is the mass fraction of (A), b is the mass fraction of (B), and c is the mass fraction of (C), and wherein 1.0>a>0, 1.0>b>0, 1.0>c>0; and with the proviso that a, b, and c fall within a region representing cubic liquid crystalline phase in combination with at least one other phase on a phase diagram representing phase behavior of (A), (B), and (C), with the proviso that the dispersion has a form of functionalized cubic liquid crystalline gel particles dispersed in the other phase.

DETAILED DESCRIPTION OF THE INVENTION

This invention relates to precursors, bulk cubic liquid crystalline gels, dispersions of cubic liquid crystalline gel particles, cubic liquid crystalline gel particles, and combinations thereof. All percentages, ratios, and proportions used herein are by weight unless otherwise specified. All measurements are made at 25° C., unless otherwise specified. All U.S. Patents and printed publications cited are herein incorporated by reference.

Definition and Usage of Terms

"Amphiphile" means a molecule with both hydrophilic and hydrophobic (lipophilic) groups (e.g, surfactants, lipids, and polymers).

"Anchor" means a small molecule, including surfactants that have a lipid-soluble 'tail' with a water-soluble 'head'. Without wishing to be bound by theory, it is thought that the role of the lipid-soluble tail is to dissolve into the bilayers of the cubic phase, and the role of the water-soluble head might be to provide a specific (or tailored) interaction such as an electrostatic or hydrogen bond with the materials of interest.

"Bulk cubic gel" means a viscous, structurally isotropic gel (clear, translucent, or opaque) having a normal, or reversed, cubic liquid crystalline structure, with a composition matching a cubic liquid crystalline region of a phase diagram representing the phase behavior of ingredients in the composition. Bulk cubic gel is also referred to herein as bulk cubic liquid crystalline gel.

"Colloidally stable" means that when cubic gel particles are dispersed in a solvent, the particles do not coalesce, flocculate, or agglomerate over some reasonable time.

"Cubic gel particles" means the dispersed form of bulk cubic gel; technically they are cubic liquid crystalline gel in equilibrium with either the solvent, isotropic liquid phase, lamellar phase, or a combination of two of these. Cubic gel particles are also referred to herein as cubic liquid crystalline gel particles.

"Cubic liquid crystalline phase material" means a composition that falls within a cubic liquid crystalline phase region on a phase diagram for the ingredients in the composition or a composition that falls within a region on the phase diagram where cubic liquid crystalline phase is in equilibrium with another phase. Cubic liquid crystalline phase material includes bulk cubic gels, cubic gel particles, and dispersions of cubic gel particles.

"Cuboplex" means a functionalized cubic liquid crystalline phase material according to this invention.

"Gel" means a Theologically semisolid system. Gel includes cubic liquid crystalline materials such as bulk cubic gels and dispersions of cubic gel particles.

"L1" means a dilute liquid phase.

"L2" means a concentrated liquid phase.

"Lipid" means any amphiphilic molecule of intermediate molecular weight that contains a substantial portion of aliphatic or aromatic hydrocarbon.

"Paste" means a liquid for topical application, preferably to the skin of an animal (preferably a human), whose viscosity is enhanced to the point that flow is largely inhibited by the presence of undissolved, as well as dissolved, solids.

"Precursor" means a formulation that will form a cubic liquid crystalline phase material upon action by a stimulus. The stimulus can be the addition of some specified material such as additional amphiphile, or solvent; the removal of some specified material such as a portion of the amphiphile, or solvent; a temperature change; a pressure change; addition of salt; or a pH change in aqueous systems.

"Stabilizer" means an agent that prevents aggregation, coalescence, and flocculation of dispersed phase particles. Stabilizers impart colloidal stability to dispersed cubic gel particles. Stabilizers include small particulates that absorb upon surfaces of the particles, ionic materials, polymers, charged lipids, surfactants, and liquid crystalline phase adsorbed to the surfaces of the particles.

"Surfactant" means an amphiphile that exhibits the following properties in water: (1) it reduces the interfacial tension, and (2) it self-assembles in solution at low concentrations.

"Tether" means a molecule larger than an anchor, including modified polymers, proteins, and enzymes that have a lipid-soluble fragment and a water-soluble fragment. Without wishing to be bound by theory, it is thought that the role of the lipid-soluble fragment is to dissolve into the bilayers of the cubic phase, and the role of the water-soluble fragment might be to provide a specific (or tailored) interaction such as an electrostatic or hydrogen bond with the materials of interest.

"Thermodynamically stable" means that a system is at its lowest energy state or a system that is kinetically trapped in the same state for some reasonable time.

Precursor

The precursor generally comprises an amphiphile capable of forming a cubic liquid crystalline phase, an optional solvent, and an additive selected from the group consisting of anchors, tethers, and/or combinations thereof. The precursor can optionally comprise an active ingredient. These constituents can also be capable of forming a hexagonal liquid crystalline phase.

Amphiphile

The amphiphile can be a single amphiphile or a combination (e.g., mixture) of two or more amphiphiles capable of forming a cubic liquid crystalline phase. Preferably, amphiphiles are surfactants capable of forming cubic liquid crystalline phases in the presence of a solvent and an additive. Suitable hydrophilic groups and methods for the selection of suitable hydrophilic groups, are disclosed in Laughlin, R. G., *The Aqueous Phase Behavior of Surfactants*, Academic Press, New York, 1994, pg. 255, and International Patent Publication WO 99/12640. Non-limiting examples of suitable amphiphiles are excerpted in Tables 1–5 below.

TABLE 1

Anionic Hydrophilic Groups

| Functional Group | General Formula |
| --- | --- |
| Alkyl carboxylate salts | $R'CO_2^-M^+$ |
| Alkanesulfonate salts | $R'SO_3^-,M^+$ |
| Alkyl sulfate salts | $R'OSO_3^-,M^+$ |
| N-Alkylsulfamate salts | $R'NHSO_3^-,M^+$ |
| Akylsulfinate salts | $R'SO_2^-,M^+$ |
| S-Alkylthiosulfate salts | $R'SSO_3^-,M^+$ |
| Phosphonate salts | $R'PO_3^-,2M^+$ |
| Phosphate monoester salts | $R'OPO_4^=,2M^+$ |
| Phosphinate salts | $R'(R')PO_2^-,M^+$ |
| Nitroamide salts | $R'N^-NO_2,M^+$ |
| Trisulfonylmethide salts | $R'SO_2(CH_3SO_2)_2C^-,M^+$ |
| Xanthate salts | $R'SCS_2^-,M^+$ |
| Phosphate diesters | |

TABLE 2

Cationic Hydrophilic Groups

| Functional Group | General Formula |
| --- | --- |
| Quaternary ammonium salts | $R'N^+(CH_3)_3,X^-$ |
| Primary, secondary, and tertiary ammonium salts | $R'N^+H_m(CH_3)_{3-m}, X^-$ |
| N-alkylpyridinium salts | $R'NC_5H_5^+,X^-$ |
| Quaternary phosphonium salts | $R'P^+(CH_3)_3,X^-$ |
| Ternary sulfonium salts | $R'S^+(CH_3)_2,X^-$ |
| Ternary sulfoxonium salts | $R'S^+(\rightarrow O)(CH_3)_2,X^-$ |
| Bis(phosphoranylidyl)ammonium salts | $[R'(CH_3)_3P\rightarrow N\leftarrow P(CH_3)_3R']^+,X^-$ |

TABLE 3

Zwitterionic Hydrophilic Groups

| Functional Group | General Formula |
| --- | --- |
| Ammonioacetates | $R'(CH_3)_2N^+CH_2CO_2^-$ |
| Ammonio hexanoates | $R'(CH_3)_2N^+(CH_2)_5CO_2^-$ |
| Ammonio alkanesulfonates | $R'(CH_3)_2N^+(CH_2)_3SO_3^-$ |
| Ammonloalkyl sulfates | $R'(CH_3)_2N^+(CH_2)NOSO_3^-$ |
| Trimethylammonio-ethyl alkylphosphonates | $R'PO_2^-OCH_2CH_2N^+(CH_3)_3$ |
| Trimethylammonio-ethylphosphate acylglyceryl esters | $R'CO_2CH_2CH(OH)CH_2OPO_2^-O(CH_2)_2N^+(CH_3)_3$ |

TABLE 4

Dipolar Hydrophilic Groups

| Functional Group | General Formula |
| --- | --- |
| Aliphatic amine oxides | $R'(CH_3)_2N\rightarrow O$ |
| Phosphine oxides | $R'(CH_3)_2P\rightarrow O$ |
| Phosphonate esters | $R'(CH_3O)_2P\rightarrow O$ |
| Phosphate esters | $R'O(CH_3O)_2P\rightarrow O$ |
| Arsine oxides | $R'(CH_3)_2As\rightarrow O$ |
| Sulfoxides | $R'(CH_3)S\rightarrow O$ |
| Sulfoximines | $R'(CH_3)S(\rightarrow O)\rightarrow NH$ |
| Sulfone diimines | $R'(CH_3)S(\rightarrow NH)_2$ |
| Ammonioamidates | $R'C(O)N-N + (CH_3)_3$ |
| Amides | $R'C(O)N(CH_3)_2$ |

TABLE 5

Single Bond Hydrophilic Groups

| Functional Group | General Formula |
| --- | --- |
| Primary Amines | $R'NH_2$ |

In Tables 1–5, R' represents a hydrocarbon group, preferably an alkyl group. M represents a metal atom. The subscript m is 1, 2, or 3. X represents a halogen atom.

Exemplary, but non-limiting, lipophilic groups include monovalent hydrocarbon groups, substituted monovalent hydrocarbon groups, fluorocarbons, and siloxanes. Suitable monovalent hydrocarbon groups have 6 to 22 carbon atoms, preferably 8 to 22 carbon atoms, and more preferably 10 to 18 carbon atoms. Substituted monovalent hydrocarbon group include halogenated monovalent hydrocarbon groups, typically having 6 to 22 carbon atoms. The monovalent hydrocarbon groups and substituted monovalent hydrocarbon groups can be saturated or unsaturated, branched or unbranched. Preferred branched hydrocarbon groups typically have 8 to 22 carbon atoms. Preferred linear hydrocarbon groups have 8 to 18 carbon atoms.

It is preferred that an amphiphile include surfactants having HLB values of about 2.1 to about 4.6. See Porter, M. R., *Handbook of Surfactants*, 2$^{nd}$ ed., Blackie Academic & Professional, pp. 188–236. Suitable monoglyceride should have sufficient purity to form cubic liquid crystalline phase in combination with solvent and the hydrotrope. A monoglyceride is typically greater than about 40% to 100% pure, preferably about 82.5 to 100% pure, however, a purity of less than about 40% may also be suitable.

A class of preferred surfactants includes monoglycerides having the general formula:

R is selected from the group consisting of monovalent hydrocarbon groups of 6 to 22 carbon atoms, preferably 8 to 22 carbon atoms, more preferably 10 to 18 carbon atoms, and monovalent halogenated hydrocarbon groups of 6 to 22 carbon atoms. The monovalent hydrocarbon groups can be saturated or unsaturated, branched or unbranched. Preferred branched hydrocarbon groups typically have 8 to 22 carbon atoms. Preferred linear hydrocarbon groups have 8 to 18 carbon atoms. Preferred monoglycerides have a melting point $\geq 40°$ C. International Patent Publication No. WO 99/12640 discloses suitable amphiphiles that can form cubic liquid crystalline phase.

Exemplary amphiphiles are disclosed in U.S. Pat. No. 5,756,108 and include 3,7,11,15-tetramethyl-1,2,3-hexadecanetriol, phytanetriol, N-2-alkoxycarbonyl derivatives of N-methylglucamine, and unsaturated fatty acid monoglycerides, monoglyceride surfactants such as glycerol monooleate (HLB of 3.8), glycerol monostearate (HLB 3.4), ethoxylated alcohol surfactants such as $C_{12}EO_2$, $C_{12}EO_{23}$, and $C_{16}EO_3$, wherein EO represents an ethylene oxide group (See Lynch et al., *Langmuir*, Vol. 16, No. 7, pp. 3537–3542 (2000)), monolinolein, and combinations thereof.

Other suitable amphiphiles can include amphoteric surfactants such as betaines, glycinates, amino propionates, and combinations thereof. Additional suitable amphiphiles include lipids of biological origin such as fatty acids, acyl glycerols, glycerolphospholipids, phosphatidic acid (and salts thereof), phosphatidylethanolamine, phosphatidylcholine (lecithin), phosphatidylserine, phosphatidyllinositol, phosphatidylethanolamine, spingolipids (Ceramides), spingomyelin, cerebroside, glucocerebroside, ganglioside, steroids, cholesterol esters (stearates, etc.), sugar-based surfactants, glucolipids, galactolipids, and combinations thereof.

Solvent

The solvent can be a single solvent or a combination of two or more polar or non-polar solvents and may contain other ingredients, such as buffers and/or stabilizers. Exemplary, but non-limiting, polar solvents include water, glycerol, polyglycols such as polyethylene glycol, formamides such as formamide, n-methyl formamide and dimethylformamide, ethylammonium nitrate, and combinations thereof. Exemplary, but non-limiting, non-polar solvents include aliphatic hydrocarbons, such as alkanes and fatty esters such as lanolin, and substituted hydrocarbons, such as halogenated hydrocarbons, and combinations thereof.

Additives

Generally, the additive is an anchor, a tether, and/or a combination thereof having a low Krafft temperature, preferably below about 25° C. to prevent crystallization. Most preferably, the anchors are selected from the group consisting of positive charged surfactants and negative charged surfactants. Examples of suitable surfactants can be found in McCutcheon, *Emulsifiers & Detergents, North American Edition*, vol. 1 (1994). Preferred positive charged surfactants include dioctyldecylamine hydrogen chloride and di(canola ethyl ester) dimethyl amine chloride. Preferred negative charged surfactants include potassium oleate. Tethers are preferably selected from the group consisting of derivatized polysaccharides and linear substituted polymers. However, the exact choice of anchor and/or tether depends on various factors including the intended use of the precursor, gel, dispersion, or particles incorporating said anchor and/or tether and any active ingredients that will be added.

There are at least two types of tethers. One type can be thought of as a large surfactant, for example, in which one end of the molecule is a lipid-soluble fragment or chain and at the other end is the added water-soluble fragment for specific functionality. A large polymeric spacer or backbone can separate these groups.

Another tether introduces a lipid-soluble fragment (e.g. aliphatic chain) that can attach to the bilayer with a water-soluble polymeric fragment that has multiple sites for interaction, for example, a polydentate ligand such as:

The image shows an exemplary charge peptide fragment that can be anchored to the bilayer (Lys=Lysine). A comparable situation can exist with polymers where Lysine is replaced with polyvinyl alcohol (PVA), as shown below. It would also be possible to replace Lysine with polyvinyl alcohol (PVA), for example:

where n is an integer from about 1 to about 50.

Preferred tethers are linear, branched, block copolymers, random copolymers, or grafted copolymers. Exemplary monomers (in mono- or co-polymer applications), anchors, and tethers are tabulated in Table 6. Alternatively, surfactants containing the hydrophilic groups in Tables 3 and 4, above may be used as a tether or active when they are not being used as an amphiphile. Tethers may also be used to colloidally stabilize liquid crystalline particles.

Preferably, the additive has a hydrophobic chain length matching the hydrophobic domain of the cubic phase to improve the effective solubility in the bilayer of the cubic phase. Further, the additive can have minimal solubility in the solvent to ensure that the additive is associated with the cubic phase rather than partitioned into the solvent. In the case of anchors, di-chain over mono-chain surfactants and lipids are preferred. In the case of a tether, a higher solvent solubility may be required than for a corresponding anchor due to potential multiple molecular attachment sites. Charged-head group surfactants, lipids, and polymers are used when desiring pH, solvent or ionic strength-triggered formulations. Additionally, additives can be selected using rules of electrostatics and hydrogen bonding, for example, selecting an additive to have an electrostatic interaction with a target such as another active ingredient. However, it can be generally preferable to maximize the charge on an anchor or a tether. Eliminating the point charge, for example, by protonating a carboxylate can maximize this charge. Further, any dielectric constant of the medium can vary according to the need. The addition of salt can increase the dielectric constant of the solution, decreasing the interaction between materials. Additionally, presence of a hydrotrope in an additive can prevent additives from crystallizing and can allow the amount of additive to be increased or broaden the range of additives that can be used.

In another embodiment, the additive can be selected to hydrogen bond with a target, for example, an active ingredient. Ethylene oxide based head group surfactants, lipids, and polymers can be used when desiring temperature-triggered 'on-demand' formulation.

TABLE 6

Examples of Additives

| Anchors | Tethers |
| --- | --- |
| Positive-Charged Surfactants | Derivatized-Polysaceharides |
| Quaternary (preferably di-chain) | Cellulose-Derivatives |
| Imidazoline-based | Hydrophobically-Modified |
| Substituted amino acids (appropriate pH) | Cellulose Esters (e.g. Emulsan) |
|  | Ethylene-oxide substituted |
| Negative-Charged Surfactants | Chitin-Derivatives |
| Alkyl carboxylates (e.g. oleate) | Starch-Derivatives |
| Modified carboxylates | Glycogen |
| Isethionates | Glycoaminoglycans |
| Phosphate Esters (mono- and di-phosphate) | Keratin Sulfate |
|  | Dermatan Sulfate |
| Alkyl sulphates | Glycoproteins |
| Sulphonates | Lignan-based polymers |
| Alkyl sulphonates | Linear-Substituted Polymers |
| Olefin sulphonates | Vinyl Polymer |
| Alkyl benzene sulphonates | Poly(acrylic acid) |
| Sulphosuccinates | Poly(acrylamide) |
| Gemini-type surfactants | Polyamine |
|  | Poly(ethylene imine) |
|  | Polyamide |
|  | Polyisocyanate |
|  | Polyester |
|  | Polyphosphonate |
|  | Poly-siloxanes |
|  | Poly-carbonates |
|  | Polyethoxylates |
|  | Poloxamers |
|  | Star Polymers (Dendrimers) |
|  | Polypeptides |
|  | poly-lysine |
|  | lipo-proteins |

Active Ingredients

The precursor described above may further comprise an active ingredient (active). An active may be one active or a combination of two or more actives. The active can be added in amounts such that bulk cubic gel made from the precursor will contain up to about 15% of active, preferably about 1 to abut 10% of active wt/wt of gel.

The active can be an agrochemical such as water-soluble and insoluble pesticides and herbicides. Pesticides and herbicides may be incorporated into the ternary system as an active ingredient with hydrotropic properties or as an active ingredient separate from the hydrotrope. Exemplary, and non-limiting, pesticides include organophosphates such as diazinon and non-organophosphates such as diclofop-methyl, terrazole, vinclozolin, atrazine, oxamyl propargite, triallate, and combinations thereof. Exemplary, and non-limiting, herbicides include atrazine, nicosulfuron, carfentrazone, imazapyr, benefin, acifluorfen, and combinations thereof.

The active ingredient can be a pharmaceutical or cosmetic compound such as a non-steroidal anti-inflammatory (e.g., ketoprofen), metronidazole, acetyl salicylic acid, clotrimazole, insulin, lidocaine, hydrochloride, nitroglycerin, prilocaine, tetracycline hydrochloride, benzylpenicillin, acyclovir, guaifenesin, melatonin, metronidazole, phenylpropanolamine, pseudophedrine hydrochloride, timolol maleate, acyclovir, hydrocortisone, minoxidil (Rogaine), sildenafil citrate (Viagra), eflornithine HCl (Vaniqua), zinc pyrithione, a skin moisturizer, and combinations thereof. The active ingredient can also be an enzyme or a nutrient such as a vitamin or mineral, such as vitamin E, C, Zinc, and/or Iron.

Figure 1:
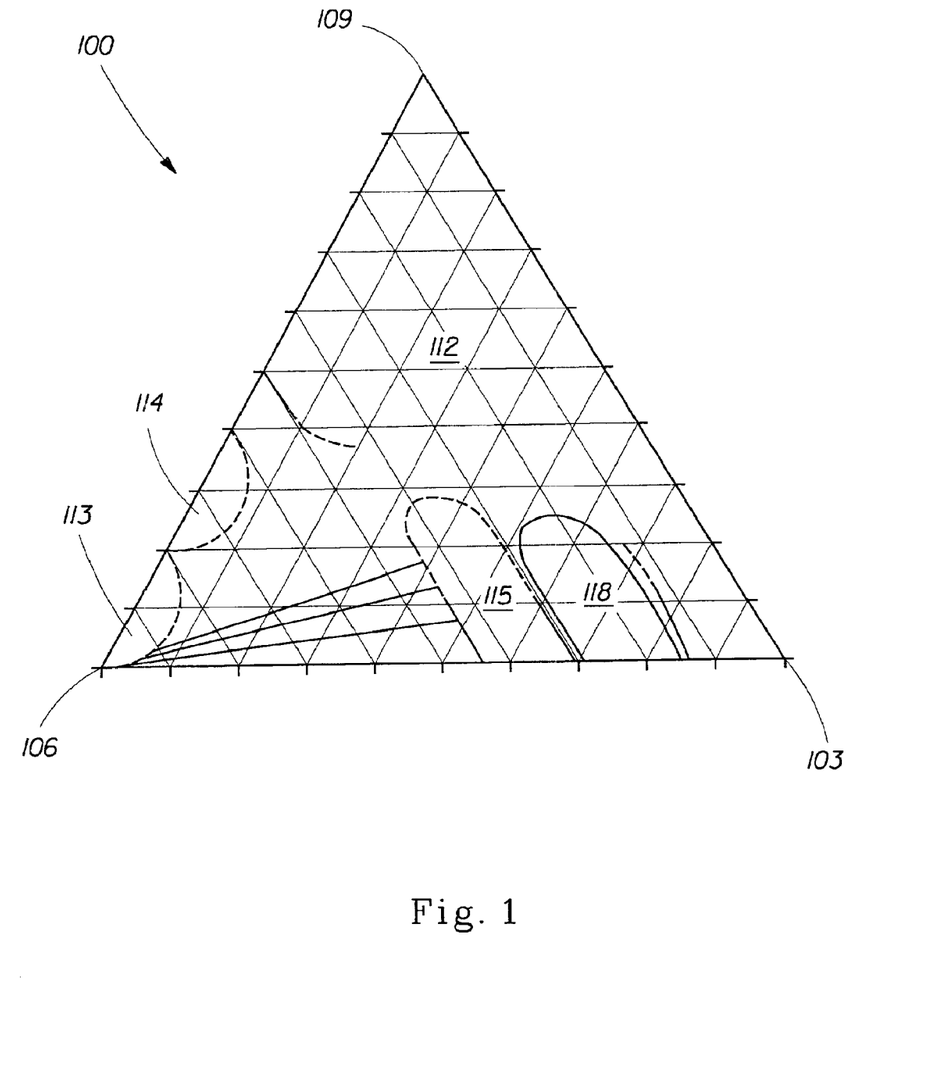
FIG. 1 is a phase diagram representing the behavior of composition containing a hydrotrope, a combination of amphiphile and additive, and a solvent.

FIG. 1 represents ternary phase diagram 100 of a ternary system of (A) monoolein 103, (B) water 106, and (C) potassiumoleate 109. Single phases (other than cubic phases) can be used as a precursor. Compositions falling in single-phase regions such as the lamellar phase region 112 and the L1 phase region 113 are suitable precursors. Compositions falling in a multiple-phase region 114 where cubic phase does not form are also suitable precursors. Compositions that do not fall in the Pn3m cubic phase region 115 and Ia3d cubic phase region 118 are suitable precursors as discussed in Luzzati et al., *J. Mol. Biol.*, 229, 540–551 (1993).

A precursor can be used in an application where cubic phase formation is desired under a certain set of conditions, for example, the presence of sweat, saliva, or other material that will change the system composition such that it is in a cubic phase region. The precursor of this invention may be used to directly form either bulk cubic gel, dispersed cubic gel particles, or a combination of the two, all depending on the desires of the formulator.

Bulk Cubic Gel and Dispersions

Ingredients (A), (B), and (C) of functionalized bulk cubic liquid crystalline gels are generally present in mass-fractional relationship so that $1.0>a>0$, $1.0>b>0$, $1.0>c>0$, and more preferably $0.8 \geq a \geq 0.5$, $0.8 \geq b \geq 0.5$, $0.1 \geq c>0$. The mass fractions of (A), (B), and (C) in cubic liquid crystalline dispersions are preferably $0.15 \geq a \geq 0.05$, $0.95 \geq b \geq 0.8$, $0.05 \geq c \geq 0.01$. Cubic liquid crystalline dispersions have the form of cubic liquid crystalline gel particles dispersed in the other phase. These constituents can also be capable of forming a bulk hexagonal liquid crystalline gel.

(A), (B), and (C) are as described supra. However, the amounts of (A), (B), and (C) differ, so that either a bulk cubic liquid crystalline gel or a cubic liquid crystalline gel dispersion forms. In the case of a bulk cubic liquid crystalline gel, the amount of each ingredient should be such that the combined ingredients form a cubic liquid crystalline phase or a cubic liquid crystalline phase in combination with one or more other phases. Without wishing to be bound by theory, it is believed that a combination of the amounts of the ingredients that fall within the cubic liquid crystalline region in the phase diagram will be suitable for this invention. An active (D) may be added to either the bulk cubic gel or cubic liquid crystalline gel dispersion. These constituents can also be capable of forming a bulk hexagonal liquid crystalline gel dispersion.

Methods for Preparing Precursors and Functionalized Cubic Phase Materials

Precursor

When (A) is a solid such as monoolein, (A), (B), (C), and (D) are preferably combined by heating (A) to a temperature greater than its melting point and then combining (e.g., mixing) with (B), (C), and (D). Alternatively, (A) can be fragmented into solid particles and then combined. However, (A), (B), (C), and (D) are preferably provided so that the precursor is an isotropic liquid at 25° C. The amount of the (D) active ingredient is sufficient such that a gel formed from the precursor contains up to about 15%, preferably about 0 to about 10 wt % based on the combined weights of (A), (B), and (C). Preferably, (A) is a liquid, and (A), (B), (C), and (D) are combined by mixing.

Bulk Cubic Liquid Crystalline Gel

Bulk cubic liquid crystalline gel can be prepared by applying a stimulus to a prepared precursor. Exemplary, but non-limiting, stimuli include temperature changes, pressure changes, the addition of a salt, pH changes, the addition of a specified material such as additional amphiphile or solvent, the removal of a specified material such as a portion of the amphiphile or solvent, and combinations thereof.

The precursor can be diluted, for example, by mixing the precursor with additional amphiphile, or solvent. A bulk cubic liquid crystalline gel can also be prepared directly by combining amounts of (A), (B), and (C) corresponding to a cubic phase region on the relevant phase diagram.

Dispersed Cubic Liquid Crystalline Gel Particles

Dispersed cubic liquid crystalline gel particles can be prepared from bulk cubic gels by adding additional solvent and fragmenting the gel, or directly from the precursors by inducing nucleation via the addition, or removal, of materials, such as solvent. The gel can be fragmented by conventional means such as subjecting the gel to shear in a shear mill, ultrasonication, micromixer dispersal, or membrane emulsification. Colloidal stabilization may be necessary following dispersion unless a colloidal stabilizer is present or an additive functioning as a colloidal stabilizer is present.

After preparing a dispersion, the particles can be isolated by any conventional means. For example, removing solvent, centrifugation, filtration, evaporation, and combinations thereof, can isolate the particles.

Methods of Use

Figure 2:
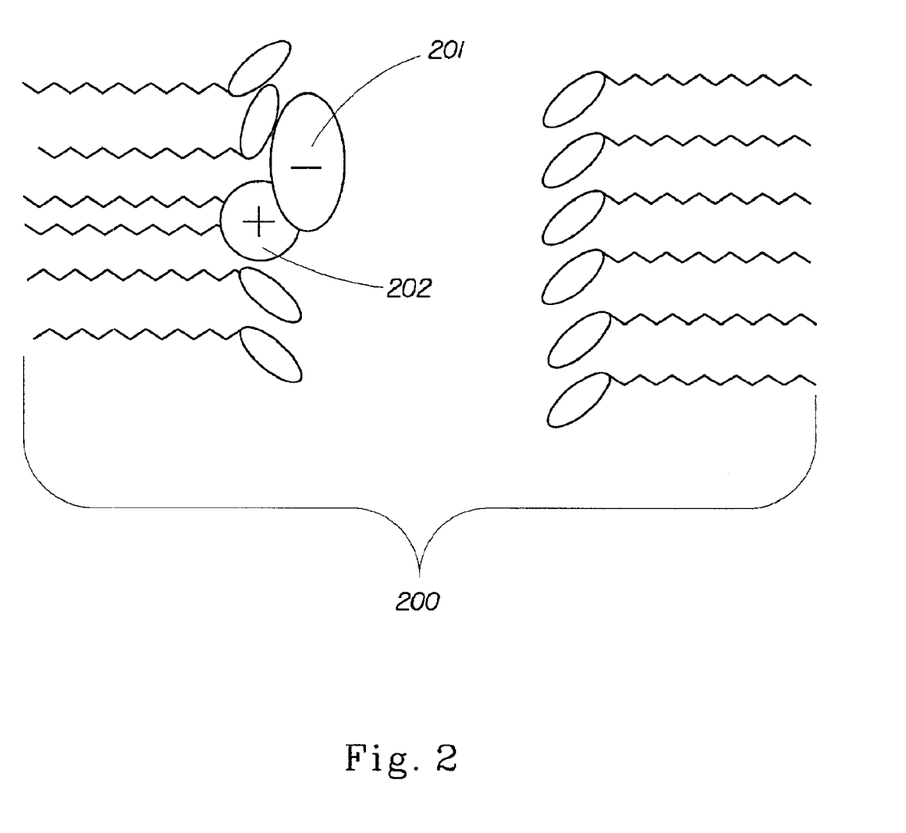
FIG. 2 represents a ketoprofen molecule in a functionalized cubic phase bilayer.

Functionalization with anchors and tethers can provide an ability to modify the interior properties of functionalized cubic liquid crystalline phase materials allowing delivery and controlled release of active ingredients. FIG. 2 illustrates a negatively charged material 201 (e.g., ionized Ketoprofen)anchored into the bicontinuous cubic liquid crystal 200 functionalized with di(canola ethyl ester) dimethylamine chloride (DEEDAC) 202. This interaction can increase the level of loading and enhances the release profile of the material. In one embodiment of the invention, the precursors, gels, dispersions, and particles can be used for topical delivery of pharmaceutical and/or cosmetic active ingredients such as Ketoprofen and those described above.

Precursors, gels, dispersions, and particles can be used for nutrient delivery, encapsulation, stabilization, and/or enzyme delivery, to generate trans-membrane protein crystal structures, and combinations thereof. Further, cuboplexes can be fabricated into mini-reactors by attaching an enzyme inside the pores that consume some biological targets, and to remove harmful compounds from their environment, such as heavy metals, which could concentrate in the aggregates and then be skimmed off wastewater.

Functionalization can offer the added ability to enhance the exterior properties of materials and can help colloidal stability. As a non-limiting example, the exterior of the cuboplexes might be modified with a charge to enhance deposition on substrates. Non-limiting examples of target substrates include skin, hair, fabric, and plant surfaces. It would also be possible to provide selective adhesion of an aggregate to biological sites by affixing an enzymatic protein to the outside of an aggregate with the aggregate containing some pharmaceutical interest. It is believed that affixing large molecules can act as a steric prevention of coalescence generated by attached polymers.

Functionalization offers the further ability to create "on demand" products. "On demand" means that the internal and external properties of a cuboplex, for example, to release or entrap materials as a consequence of a stimulus. Non-limiting releases or entrapments may be instigated by pH (charged species with a defined pKa), by the addition of salt (reduce the shielding of electrostatics), by the introduction of dielectric solvents (minimize the role of electrostatics), or by the addition or selective removal of components that can selectively bind to the regions.

Preferably, the controlled release delivery of active ingredients, including agrochemicals such as herbicides and pesticides, to a substrate, such as a plant or insect, surface can be performed using the cubic gel precursors by evaporation and/or dilution. Evaporation and/or dilution processes produce "responsive" liquids that provide targeted delivery of active ingredients in response to a stimulus, such as dilution by residual moisture or evaporation as a consequence of spraying. A line drawn from a starting point to an ending point on the phase diagram may represent evaporation and dilution processes.

EXAMPLES

Polarized Light Microscopy (PLM)

Polarized light microscopy (PLM) was used to determine whether the composition exhibits birefringence or distinct textures. PLM was carried out on a polarized light microscope or constructed light box, as described by Laughlin, R. G., *J. Colloid Interface Sci.*, 55, 239–242 (1976). Rheological properties of the composition were also observed. Compositions containing a viscous phase that exhibits no birefringence and no distinct textures by PLM can be capable of forming cubic phase.

Cryo-transmission Electron Microscopy (Cryo-TEM)

Samples were evaluated by cryo-TEM to determine whether cubic phase formed in a sample. Cryo-TEM samples were prepared in a controlled environment vitrification system (CEVS), described by Bellare, J. R., Davis, H. T., Scriven, L. E., Talmon, Y., "Controlled environment vitrification technique", *J. Electron Microsc. Tech.*, 1988, 10, 87–111.

Small Angle X-ray Scattering (SAXS)

SAXS is an excellent technique to confirm the structure of the liquid crystals because SAXS patterns are unique for each type of liquid crystal. Exemplary SAXS patterns for liquid crystal phases are given in Luzzati, V., Tardieu, A., Gulik-Kryzwicki, T., Rivas, E., Riess-Husson, F., *Nature*, 1968, 220, 485–488. For cubic phase symmetry, a plot of peak position versus $\sqrt{h^2+k^2+l^2}$ generates a straight line having a slope inversely proportional to the lattice parameter confirming the presence of cubic phase liquid crystals. The following are typical reflections for cubic phase symmetry: $P_{n3m}$: [110], [111], [200], [211], [220], and [221]; $I_{a3d}$: [211], [220], [321], [400], [420], and [332].

Example 1

Creating Cuboplex

Positively-charged Cuboplex Gels

Cuboplex gels were made from 0.16%, 0.32%, 0.57%, 0.95%, 1.22%, and 3.92% of dioctyldecyl amine hydrogen chloride (DOAC*HCl) prepared in 70:30% w/w fractions of monoolein to water. All samples were measured by SAXS to determine cuboplex structure and PLM to confirm a lack of birefringence. Comparable gels were made with the inclusion of the di(canola ethyl ester) dimethyl amine chloride (DEEDAC) and ketoprofen at higher concentrations. Surprisingly, DEEDAC can be included to levels greater than 20%.

Negatively-charged Cuboplex Gels

Negatively charged cuboplex gels were made by mixing 4% potassium oleate (KOl) into a mixture of 60%:40% monoolein and water. The gel was measured by SAXS to determine the structure of the resulting cuboplex.

Negatively-charged Cuboplex Dispersion

Base cuboplex gels were prepared by melting 1.21433 g of monoolein in a small ampule in a 40° C. water bath. A 0.20725 g KOl mixture (40% w/w potassium oleate in water) was added with a small amount of water to facilitate mixing. The mixtures were stirred, vortexed and centrifuged to a homogeneous mixture. A 2% w/w dispersion was prepared by adding water and sonicating the mixture for 1 hour. The mixture was analyzed by Cryo-TEM.

Example 2

Enhanced Absorption into Cuboplex Using Amine-base Anchors

Cubic phase liquid crystals were prepared from mixtures of water, monoolein. Several cationic surfactants (i.e., dioctadecyl dimethyl ammonium chloride (DODMAC), dioctadecyl ammonium chloride (DOAC), and di(canola ethyl ester) dimethyl amine chloride (DEEDAC)) were incorporated into the bicontinuous cubic phase liquid crystals to create a positively charged surface. The effect of the surfactant on the loading of ionized ketoprofen was assessed by measuring the partition differences of the actives with and without the inclusion of surfactant. Dioctadecyl dimethyl ammonium chloride and Dioctadecyl dihydrogen ammonium chloride were formulated into the cuboplex by dissolving the surfactant into liquid monoolein. Dioctadecyl dihydrogen ammonium chloride was also formulated into cubic phase as described supra. The effect of the surfactant on the loading of ionized ketoprofen was assessed by measuring the partition differences of the actives between the gel and an adjacent buffer with and without the inclusion of surfactant. Without wishing to be bound by theory, it is believed that inclusion of the surfactant increased the amount of active in the gels by an amount proportional to the amount of surfactant.

Example 3

Stabilized Dispersed Cuboplex Using Charge Oleate-based Repulsion

A mixture of potassium oleate (0.20730 g), water (0.60817 g) and monoolein (1.21320 g) was used as a stock solution to make 2% dispersion in water. A sample containing the stock mixture (0.06963g) diluted to 2% with water was prepared and sonicated for 3 hours to form a cuboplex dispersion. The control mixture was a 2% dispersion of monoolein and $H_2O$ that was sonicated for 3 hours to form cubosome dispersion.

Example 4

Electrolyte-based Change in Colloid Stability (Flocculation)

A stock gel of oleate-containing cuboplex was prepared by mixing 0.20725 g of potassium oleate with 1.000 g of monoolein. A small amount of water was added to facilitate mixing. The sample was centrifuged and mixed several times on a vortex to thoroughly mix the sample.

Solutions were prepared at different electrolyte concentrations by adding different amounts of KCl stock solution to these mixtures, as described by the following table, and sonicated for 5 hours in a temperature-controlled bath.

TABLE 7

KCl Concentrations Used to Prepare Different Electrolyte Concentrations

| Concentration of KCl | Amount KCl Solution | Amount KOl-MO Mixture |
|---|---|---|
| $10^{-2}$ M | 10 ml | 0.19886 g |
| $10^{-3}$ M | 10 ml | 0.20017 g |
| $10^{-4}$ M | 10 ml | 0.20248 g |
| $10^{-5}$ M | 10 ml | 0.20248 g |
| $10^{-6}$ M | 10 ml | 0.20175 g |

Without wishing to be bound by theory, it is believed that traditional principles of colloid science would show the dispersion flocculating readily at high salt concentrations, but remaining stable at low salt concentrations.

Example 5 pH-based On-demand Change in Colloid Stability (of Flocculation) Properties Using Oleate-based Electrostatics A mixture of potassium oleate (0.20730 g), water (0.60817 g) and monoolein (1.21320 g) was used as a stock solution to make 2% dispersions in water. The first dispersion contained 0.06963 g stock solution diluted with 2% of 0.01 molar phosphate buffer @ pH=10. The second dispersion was a 2% mixture of stock solution in pH=7 buffer. The third dispersion was a 2% mixture of stock solution in pH=4 buffer. All samples were sonicated for 3 hours and photographed. Without desiring to be bound by theory, it is believed that the dispersions flocculate at lower pH values where hydrogen bonding can readily occur. Additional dispersions were produced and dried to remove water. IR was used to determine ionization state and overall bonding of carboxylic acid-carboxylate systems of the additional dispersions.

Example 6

Kinetic Modifications Associated with Functionalization

A 50 ml graduated cylinder was modified to lower the height of the edges and flatten the bottom. An experiment was developed to independently measure the diffusion of materials through a cubic phase gel by adding an active to the monoolein-based cubic phase placed at the bottom of a reaction vessel. 0.5 g of monoolein was melted and added to the bottom of the graduated cylinder. From 0.1 to 0.01 g of ketoprofen was dissolved in monoolein and 0.03 g of stearic acid was added. 0.4 g of pH=10 buffer was added to the mixture to ensure formation of a homogeneous gel. The cylinder was then centrifuged.

An excess of 50 ml buffer was added to the top of the gel at the start of the diffusion experiment. A stirrer was inserted into the top of the vessel to add convection into the buffer above the solution. A representative sample was removed and analyzed by UV-VIS to determine the concentration. A control sample was prepared without stearic acid. Similarly, DEEDAC was formulated into gels and found to significantly retard the release of ionized ketoprofen from the resulting gels.

While particular embodiments of the present invention have been illustrated and described, it will be obvious to those skilled in the art that various changes and modifications may be made without departing from the spirit and scope of the invention. One skilled in the art will also be able to recognize that the scope of the invention also encompasses interchanging various features of the embodiments illustrated and described above. Accordingly, the appended claims are intended to cover all such modifications that are within the scope of the invention.

We claim:

1. A bulk cubic liquid crystalline gel suitable for topical application to skin, hair, fabric, and plant surfaces, for the delivery of pharmaceutical and/or cosmetic active ingredients consisting essentially of:
   (A) an amphiphile comprising a monoglyceride capable of forming a cubic liquid crystalline phase;
   (B) a polar solvent; and
   (C) an additive selected from the group consisting of an ionic anchor, a tether, and combinations thereof, and wherein (A), (B), and (C) are present in mass fractions relative to each other such that $$1.0 = a+b+c$$

wherein a is the mass fraction of (A), b is the mass fraction of (B), and c is the mass fraction of (C), and wherein the mass-fractional relationship between a, b and c is 0.8>a>0.5, 0.8>b>0.5, 0.1>c>0; and with the proviso that a, b, and c fall within a cubic liquid crystalline phase region on a phase diagram representing phase behavior of (A), (B), and (C).

2. The bulk cubic liquid crystalline gel of claim 1 further comprising an active ingredient (D), wherein the active ingredient is a pharmaceutical or cosmetic compound selected from the group consisting of non-steroidal anti-inflammatory drugs, metronidazole, acetyl salicylic acid, clotrimazole, insulin, lidocaine hydrochloride, nitroglycerin, prilocaine, tetracycline hydrochloride, benzylpenicillin, acyclovir, guaifenesin, melatonin, metronidazole, phenylpropanolamine, pseudoephedrine hydrochloride, timolol maleate, acyclovir, hydrocortisone, minoxidil, sildenafil citrate, eflornithine HCl, zinc pyrithione, a skin moisturizer, vitamins, minerals, and combinations thereof.

3. A dispersion of cubic liquid crystalline gel particles suitable for topical application to skin, hair, fabric, and plant surfaces, for the delivery of pharmaceutical and/or cosmetic active ingredients consisting essentially of:
   (A) an amphiphile comprising a monoglyceride capable of forming a cubic liquid crystalline phase;
   (B) a polar solvent; and
   (C) an additive selected from the group consisting of an ionic anchor, a tether, and combinations thereof;
   wherein (A), (B), and (C) are present in mass fractions relative to each other such that $$1.0 = a+b+c$$

wherein a is the mass fraction of (A), b is the mass fraction of (B), and c is the mass fraction of (C), and wherein the mass-fractional relationship between a, b and c is 0.15>a>0.05, 0.95>b>0.8, 0.05>c>0.01; and with the proviso that a, b, and c fall within a region representing cubic liquid crystalline phase in combination with at least one other phase on a phase diagram representing phase behavior of (A), (B), and (C), with the proviso that the dispersion has a form of functionalized cubic liquid crystalline gel particles dispersed in the other phase.

4. A cubic liquid crystalline phase precursor suitable for topical application to skin, hair, fabric, and plant surfaces, for the delivery of pharmaceutical and/or cosmetic active ingredients consisting essentially of:
   A) an amphiphile comprising a monoglyceride, which is capable of forming a cubic liquid crystalline phase;
   B) a polar solvent selected from the group consisting of water, glycerol, glycols, formamides, ethylammonium nitrate, and combinations thereof; and
   C) an additive selected from the group consisting of an ionic anchor, wherein (A), (B), and (C) are present in mass fractions relative to each other such that $$1.0 = a+b+c$$

wherein a is the mass fraction of (A), b is the mass fraction of (B), and c is the mass fraction of (C), and, wherein the mass-fractional relationship of a, b and c is $0.8 \geq a \geq 0.5$, $0.8 \geq b \geq 0.5$, $0.1 \geq c > 0$.

5. A method for preparing the cubic liquid crystalline phase precursor of claim 4 suitable for topical application to skin, hair, fabric, and plant surfaces, for the delivery of pharmaceutical and/or cosmetic active ingredients, (B), (C) and (D) an active ingredient, wherein (A), (B), and (C) are present in mass fractions relative to each other such that $$1.0 = a+b+c$$

wherein a is the mass fraction of (A), b is the mass fraction of (B), and c is the mass fraction of (C), and wherein the mass-fractional relationship between a, b and c is $0.8 \geq a \geq 0.5$, $0.8 \geq b \geq 0.5$, $0.1 \geq c > 0$; and with the proviso that a, b, and c do not fall within a cubic liquid crystalline phase region on a phase diagram representing phase behavior of (A), (B), and (C), and with the proviso that amounts of each ingredient in the composition are such that a cubic liquid crystalline phase forms upon occurrence of a stimulus, and wherein the active ingredient is a pharmaceutical or cosmetic compound selected from the group consisting of non-steroidal anti-inflammatory drugs, metronidazole, acetyl salicylic acid, clotrimazole, insulin, lidocaine hydrochloride, nitroglycerin, prilocaine, tetracycline hydrochloride, benzylnenicillin, acyclovir, guaifenesin, melatonin, metronidazole, phenylpropanolamine, pseudoephedrine hydrochloride, timolol maleate, acyclovir, hydrocortisone, minoxidil, sildenafil citrate, eflornithine HCl, zinc pyrithione, a skin moisturizer, vitamins, minerals, and combinations thereof.

6. The method of claim 5, wherein (A) is a liquid, and ingredients (A), (B), and (C), and (D) are combined by mixing.

7. The method of claim 5, wherein (A) is a solid, and (A), (B), (C), and (D) are combined by a method selected from the group consisting of:
  (a) heating (A) to a temperature greater than its melting point and then mixing (A) with ingredients (B), (C), and (D); and
  (b) fragmenting (A) into solid particles and thereafter combining (A) and (B), (C), and (D).

8. The method of claim 5, wherein the stimulus is selected from the group consisting of:
  (a) addition of a specified material selected from the group consisting of additional amphiphile and solvent;
  (b) removal of a material selected from the group consisting of a portion of the amphiphile, and solvent;
  (c) a temperature change;
  (d) a pH change;
  (e) addition of a salt;
  (f) a pressure change; and
  (g) combinations thereof.

9. The precursor of claim 4, wherein the monoglyceride is of the formula:

wherein R is selected from the group consisting of monovalent hydrocarbon groups of 6 to 22 carbon atoms, and monovalent halogenated hydrocarbon groups of 6 to 22 carbon atoms.

10. The precursor of claim 4, wherein (C) is an ionic anchor selected from the group consisting of positively charged surfactants and negatively charged surfactants.

11. The precursor of claim 10, wherein the anchor is a positively charged surfactant selected from the group consisting of quaternary surfactants, imidazoline based surfactants, substituted amino acids, and combinations thereof.

12. The precursor of claim 10, wherein the anchor is a negatively charged surfactant selected from the group consisting of alkyl carboxylates, modified carboxylates, isetbionates, mono- and di-phosphate esters, alkyl sulphates, sulphonates, alkyl sulphonates, olefin sulphonates, alkyl benzene sulphonates, sulphosuccinates, and combinations thereof.

13. The precursor of claim 4 further comprising (D), an active ingredient, wherein the active ingredient is a pharmaceutical or cosmetic compound selected from the group consisting of non-steroidal anti-inflammatory drugs, metronidazole, acetyl salicylic acid, clotrimazole, insulin, lidocaine hydrochloride, nitroglycerin, prilocaine, tetracycline hydrochloride, benzylpenicillin, acyclovir, guaifenesin, melatonin, metronidazole, phenylpropanolamine, pseudoephedrine hydrochloride, timolol maleate, acyclovir, hydrocortisone, minoxidil, sildenafil citrate, eflornithine HCl, zinc pyrithione, a skin moisturizer, vitamins, minerals, and combinations thereof.

14. A cubic liquid crystalline phase precursor suitable for topical application to skin, hair, fabric, and plant surfaces, for the delivery of pharmaceutical and/or cosmetic active ingredients consisting essentially of:
  A) an amphiphile comprising a monoglyceride, which is capable of forming a cubic liquid crystalline phase;
  B) a polar solvent selected from the group consisting of water, glycerol, glycols, formamides, ethylammonium nitrate, and combinations thereof; and
  C) an additive selected from the group consisting of tethers, and wherein (A), (B), and (C) are present in mass fractions relative to each other such that $1.0 = a + b + c$ wherein a is the mass fraction of (A), b is the mass fraction of (B), and c is the mass fraction of (C), and, wherein the mass-fractional relationship is $0.8 \geq a \geq 0.5$, $0.8 \geq b \geq 0.5$, $0.1 \geq c > 0$.

15. The precursor of claim 14, wherein the monoglyceride is of the formula:

wherein R is selected from the group consisting of monovalent hydrocarbon groups of 6 to 22 carbon atoms, and monovalent halogenated hydrocarbon groups of 6 to 22 carbon atoms.

16. The precursor of claim 14, wherein (C) is a tether selected from the group consisting of derivatized polysaccharides, linear substituted polymers, star polymers, polypeptides, and polynucleotides, and combinations thereof.

17. The precursor of claim 16, wherein the tether is a derivatized polysaccharide selected from the group consisting of cellulose derivatives, chitin derivatives, starch derivatives, glycogen, glycoaminogylcans, lignan-based polymers, and combinations thereof.

18. The precursor of claim 16, wherein the tether is a linear substituted polymer selected from the group consisting of vinyl polymers, polyamines, polyamides, polyesters, polyphosphates, polysiloxanes, polycarbonates, polyethoxylates, and combinations thereof.

19. The precursor of claim 16, wherein the tether is a polypeptide selected from the group consisting of polylysine, lipoproteins, and combinations thereof.

20. The precursor of claim 14 further comprising (D), an active ingredient, wherein the active ingredient is a pharmaceutical or cosmetic compound selected from the group consisting of non-steroidal anti-inflammatory drugs, metronidazole, acetyl salicylic acid, clotrimazole, insulin, lidocaine hydrochloride, nitroglycerin, prilocaine, tetracycline hydrochloride, benzylpenicillin, acyclovir, guaifenesin, melatonin, metronidazole, phenylpropanolamine, pseudoephedrine hydrochloride, timolol maleate, acyclovir, hydrocortisone, minoxidil, sildenafil citrate, eflornithine HCl, zinc pyrithione, skin moisturizers, vitamins, minerals, and combinations thereof.

21. A cubic liquid crystalline phase precursor suitable for topical application to skin, hair, fabric, and plant surfaces, for the delivery of pharmaceutical and/or cosmetic active ingredients consisting essentially of:
  A) an amphiphile comprising a monoglyceride, which is capable of forming a cubic liquid crystalline phase;
  B) a polar solvent selected from the group consisting of water, glycerol, glycols, formamides, ethylammonium nitrate, and combinations thereof; and C) an additive selected from the group consisting of an ionic anchors, and wherein (A), (B), and (C) are present in mass fractions relative to each other such that $1.0 = a+b+c$ wherein a is the mass fraction of (A), b is the mass fraction of (B), and c is the mass fraction of (C), and, wherein the mass-fractional relationship between a, b and c is $0.15 \geq a \geq 0.05$, $0.95 \geq b \geq 0.8$, $0.05 \geq c \geq 0.01$.

22. The precursor of claim 21, wherein the monoglyceride is of the formula:

wherein R is selected from the group consisting of monovalent hydrocarbon groups of 6 to 22 carbon atoms, and monovalent halogenated hydrocarbon groups of 6 to 22 carbon atoms.

23. The precursor of claim 21, wherein (C) is an ionic anchor selected from the group consisting of positively charged surfactants and negatively charged surfactants.

24. The precursor of claim 23, wherein the anchor is a positively charged surfactant selected from the group consisting of quaternary surfactants, imidazoline based surfactants, substituted amino acids, and combinations thereof.

25. The precursor of claim 23, wherein the anchor is a negatively charged surfactant selected from the group consisting of alkyl carboxylates, modified carboxylates, isethionates, mono- and di-phosphate esters, alkyl sulphates, sulphonates, alkyl sulphonates, olefin sulphonates, alkyl benzene sulphonates, sulphosuccinates, and combinations thereof.

26. The precursor of claim 21 further comprising (D), an active ingredient wherein the active ingredient is a pharmaceutical or cosmetic compound selected from the group consisting of non-steroidal anti-inflammatory drugs, metronidazole, acetyl salicylic acid, clotrimazole, insulin, lidocaine hydrochloride, nitroglycerin, prilocaine, tetracycline hydrochloride, benzylpenicillin, acyclovir, guaifenesin, melatonin, metronidazole, phenylpropanolamine, pseudoephedrine hydrochloride, timolol maleate, acyclovir, hydrocortisone, minoxidil, sildenafil citrate, eflornithine HCl, zinc pyrithione, skin moisturizers, vitamins, minerals, and combinations thereof.

27. A cubic liquid crystalline phase precursor suitable for topical application to skin, hair, fabric, and plant surfaces, for the delivery of pharmaceutical and/or cosmetic active ingredients consisting essentially of:

A) an amphiphile comprising a monoglyceride, which is capable of forming a cubic liquid crystalline phase;

B) a polar solvent selected from the group consisting of water, glycerol, glycols, formamides, ethylammonium nitrate, and combinations thereof; and

C) an additive selected from the group consisting of tethers, and wherein (A), (B), and (C) are present in mass fractions relative to each other such that $1.0 = a+b+c$ wherein a is the mass fraction of (A), b is the mass fraction of (B), and c is the mass fraction of (C), and, wherein the mass-fractional relationship between a, b and c is $0.15 \geq a \geq 0.05$, $0.95 \geq b \geq 0.8$, $0.05 \geq c \geq 0.01$.

28. The precursor of claim 27, wherein the monoglyceride is of the formula:

wherein R is selected from the group consisting of monovalent hydrocarbon groups of 6 to 22 carbon atoms, and monovalent halogenated hydrocarbon groups of 6 to 22 carbon atoms.

29. The precursor of claim 27, wherein (C) is a tether selected from the group consisting of derivatized polysaccharides, linear substituted polymers, star polymers, polypeptides, and polynucleotides, and combinations thereof.

30. The precursor of claim 29, wherein the tether is a derivatized polysaccharide selected from the group consisting of cellulose derivatives, chitin derivatives, starch derivatives, glycogen, glycoaminogylcans, lignan-based polymers, and combinations thereof.

31. The precursor of claim 29, wherein the tether is a linear substituted polymer selected from the group consisting of vinyl polymers, polyamines, polyamides, polyesters, polyphosphates, polysiloxanes, polycarbonates, polyethoxylates, and combinations thereof.

32. The precursor of claim 29, wherein the tether is a polypeptide selected from the group consisting of polylysine, lipoproteins, and combinations thereof.

33. The precursor of claim 27 further comprising (D), an active ingredient, wherein the active ingredient is a pharmaceutical or cosmetic compound selected from the group consisting of non-steroidal anti-inflammatory drugs, metronidazole, acetyl salicylic acid, clotrimazole, insulin, lidocaine hydrochloride, nitroglycerin, prilocaine, tetracycline hydrochloride, benzylpenicillin, acyclovir, guaifenesin, melatonin, metronidazole, phenylpropanolamine, pseudoephedrine hydrochloride, timolol maleate, acyclovir, hydrocortisone, minoxidil, sildenafil citrate, eflornithine HCl, zinc pyrithione, skin moisturizers, vitamins, minerals, and combinations thereof.

34. A cubic liquid crystalline phase precursor suitable for topical application to skin, hair, fabric, and plant surfaces, for the delivery of pharmaceutical and/or cosmetic active ingredients consisting essentially of:

A) an amphiphile comprising a monoglyceride, which is capable of forming a cubic liquid crystalline phase;

B) a polar solvent selected from the group consisting of water, glycerol, glycols, formamides, ethylammonium nitrate, and combinations thereof; and C) an additive selected from the group consisting of an ionic anchor, and wherein (A), (B), and (C) are present in mass fractions relative to each other such that $1.0 = a+b+c$ wherein a is the mass fraction of (A), b is the mass fraction of (B), and c is the mass fraction o (C), and, wherein the mass-fractional relationship is between a, b and c is $1.0 > a > 0.7$, $0.30 \geq b > 0$, $0.01 > c > 0$.

35. The precursor of claim 34, wherein the monoglyceride is of the formula:

wherein R is selected from the group consisting of monovalent hydrocarbon groups of 6 to 22 carbon atoms, and monovalent halogenated hydrocarbon groups of 6 to 22 carbon atoms.

36. The precursor of claim 34, wherein (C) is an ionic anchor selected from the group consisting of positively charged surfactants and negatively charged surfactants.

37. The precursor of claim 36, wherein the anchor is a positively charged surfactant selected from the group consisting of quaternary surfactants, imidazoline based surfactants, substituted amino acids, and combinations thereof.

38. The precursor of claim 36, wherein the anchor is a negatively charged surfactant selected from the group consisting of alkyl carboxylates, modified carboxylates, isethionates, mono- and di-phosphate esters, alkyl sulphates, sulphonates, alkyl sulphonates, olefin sulphonates, alkyl benzene sulphonates, sulphosuccinates, and combinations thereof.

39. The precursor of claim 34 further comprising (D), an active ingredient, wherein the active ingredient is a pharmaceutical or cosmetic compound selected from the group consisting of non-steroidal anti-inflammatory drugs, metronidazole, acetyl salicylic acid, clotrimazole, insulin, lidocaine hydrochloride, nitroglycerin, prilocaine, tetracycline hydrochloride, benzylpenicillin, acyclovir, guaifenesin, melatonin, metronidazole, phenylpropanolamine, pseudoephedrine hydrochloride, timolol maleate, acyclovir, hydrocortisone, minoxidil, sildenafil citrate, eflornithine HCl, zinc pyrithione, skin moisturizers, vitamins, minerals, and combinations thereof.

40. A cubic liquid crystalline phase precursor suitable for topical application to skin, hair, fabric, and plant surfaces, for the delivery of pharmaceutical and/or cosmetic active ingredients consisting essentially of:

A) an amphiphile comprising a monoglyceride, which is capable of forming a cubic liquid crystalline phase;

B) a polar solvent selected from the group consisting of water, glycerol, glycols, formamides, ethylammonium nitrate, and combinations thereof, and C) an additive selected from the group consisting of tethers, and wherein (A), (B), and (C) are present in mass fractions relative to each other such that $$1.0 = a+b+c$$

wherein a is the mass fraction of (A), b is the mass fraction of (B), and c is the mass fraction of (C), and, wherein the mass-fractional relationship between a, b and c is $1.0 > a > 0.7$, $0.30 \geq b > 0$, $0.1 > c > 0$; and wherein the precursor is used for topical application to skin, hair, fabric, and plant surfaces, for the delivery of pharmaceutical and/or cosmetic active ingredients.

41. The precursor of claim 40, wherein the monoglyceride is of the formula:

wherein R is selected from the group consisting of monovalent hydrocarbon groups of 6 to 22 carbon atoms, and monovalent halogenated hydrocarbon groups of 6 to 22 carbon atoms.

42. The precursor of claim 40, wherein (C) is a tether selected from the group consisting of derivatized polysaccharides, linear substituted polymers, star polymers, polypeptides, and polynucleotides, and combinations thereof.

43. The precursor of claim 42, wherein the tether is a derivatized polysaccharide selected from the group consisting of cellulose derivatives, chitin derivatives, starch derivatives, glycogen, glycoaminogylcans, lignan-based polymers, and combinations thereof.

44. The precursor of claim 42, wherein the tether is a linear substituted polymer selected from the group consisting of vinyl polymers, polyamines, polyamides, polyesters, polyphosphates, polysiloxanes, polycarbonates, polyethoxylates, and combinations thereof.

45. The precursor of claim 42, wherein the tether is a polypeptide selected from the group consisting of polylysine, lipoproteins, and combinations thereof.

46. The precursor of claim 40 further comprising (D), an active ingredient, wherein the active ingredient is a pharmaceutical or cosmetic compound selected from the group consisting of non-steroidal anti-inflammatory drugs, metronidazole, acetyl salicylic acid, clotrimazole, insulin, lidocaine hydrochloride, nitroglycerin, prilocaine, tetracycline hydrochloride, benzylpenicillin, acyclovir, guaifenesin, melatonin, metronidazole, phenylpropanolamine, pseudoephedrine hydrochloride, timolol maleate, acyclovir, hydrocortisone, minoxidil, sildenafil citrate, eflornithine HCl, zinc pyrithione, skin moisturizers, vitamins, minerals, and combinations thereof.

47. A cubic liquid crystalline phase precursor suitable for topical application to skin, hair, fabric, and plant surfaces, for the delivery of pharmaceutical and/or cosmetic active ingredients consisting essentially of:

A) an amphiphile selected from the group consisting of 3,7,11,15-tetramethyl-1,2,3-hexadecanetriol, phytanetriol, N-2-alkoxycarbonyl derivatives of N-methylglucamine, unsaturated fatty acid monoglycerides, glycerol monooleate, glycerol monostearate, monolinolein, monoolein, $C_{12}EO_2$, $C_{12}EO_{23}$, and $C_{16}EO_3$, wherein EO represents an ethylene oxide group, and combinations thereof which are capable of forming a cubic liquid crystalline phase;

B) a polar solvent selected from the group consisting of water, glycerol, glycols, formamides, ethylammonium nitrate, and combinations thereof; and C) an additive selected from the group consisting of ionic anchors and tethers, wherein the ionic anchors are selected from dioctyldecylamine hydrogen chloride, di(canola ethyl ester) dimethyl amine chloride, and potassium oleate, and mixtures thereof, and the tether is selected from derivatized polysaccharides and linear substituted polymers and mixtures thereof;

wherein (A), (B), and (C) are present in mass fractions relative to each other such that $$1.0 = a+b+c$$

wherein a is the mass fraction of (A), b is the mass fraction of (B), and c is the mass fraction of (C), and the mass-fractional relationship between a, b and c is $0.8 \geq a \geq 0.5$, $0.8 \geq b \geq 0.5$, $0.1 \geq c > 0$.

48. The precursor of claim 47 further comprising (D), an active ingredient selected from the group consisting of non-steroidal anti-inflammatory drugs, metronidazole, acetyl salicylic acid, clotrimazole, insulin, lidocaine hydrochloride, nitroglycerin, prilocaine, tetracycline hydrochloride, benzylpenicillin, acyclovir, guaifenesin, melatonin, metronidazole, phenylpropanolamine, pseudoephedrine hydrochloride, timolol maleate, acyclovir, hydrocortisone, minoxidil, sildenafil citrate, eflornithine HCl, zinc pyrithione, skin moisturizers, vitamins, minerals, and combinations thereof.

49. A cubic liquid crystalline phase precursor suitable for topical application to skin, hair, fabric, and plant surfaces, for the delivery of pharmaceutical and/or cosmetic active ingredients consisting essentially of:
   A) an amphiphile selected from the group consisting of 3,7,11,15-tetramethyl-1,2,3-hexadecanetriol, phytanetriol, N-2-alkoxycarbonyl derivatives of N-methylglucamine, unsaturated fatty acid monoglycerides, glycerol monooleate, glycerol monostearate, monolinolein, monoolein, $C_{12}EO_2$, $C_{12}EO_{23}$, and $C_{16}EO_3$, wherein EO represents an ethylene oxide group, and combinations thereof, which are capable of forming a cubic liquid crystalline phase;
   B) a polar solvent selected from the group consisting of water, glycerol, glycols, formamides, ethylammonium nitrate, and combinations thereof; and
   C) an additive selected from the group consisting of ionic anchors and tethers, wherein the ionic anchors are selected from dioctyldecylamine hydrogen chloride, di(canola ethyl ester) dimethyl amine chloride, and potassium oleate, and mixtures thereof and the tether is selected from derivatized polysaccharides and linear substituted polymers and mixtures thereof;
   wherein (A), (B), and (C) are present in mass fractions relative to each other such that $$1.0 = a+b+c$$

wherein a is the mass fraction of (A), b is the mass fraction of (B), and c is the mass fraction of (C), and the mass-fractional relationship between a, b and c is $0.15 \geq a \geq 0.05$, $0.95 \geq b \geq 0.8$, $0.05 \geq c \geq 0.01$;
   and wherein the precursor is used for topical application to skin, hair, fabric, and plant surfaces, for the delivery of pharmaceutical and/or cosmetic active ingredients.

50. The precursor of claim 49 further comprising (D), an active ingredient selected from the group consisting of non-steroidal anti-inflammatory drugs, metronidazole, acetyl salicylic acid, clotrimazole, insulin, lidocaine hydrochloride, nitroglycerin, prilocaine, tetracycline hydrochloride, benzylpenicillin, acyclovir, guaifenesin, melatonin, metronidazole, phenylpropanolamine, pseudoephedrine hydrochloride, timolol maleate, acyclovir, hydrocortisone, minoxidil, sildenafil citrate, eflornithine HCl, zinc pyrithione, skin moisturizers, vitamins, minerals, and combinations thereof.

51. A cubic liquid crystalline phase precursor suitable for topical application to skin, hair, fabric, and plant surfaces, for the delivery of pharmaceutical and/or cosmetic active ingredients consisting essentially of:
   A) an amphiphile selected from the group consisting of 3,7,11,15-tetramethyl-1,2,3-hexadecanetriol, phytanetriol, N-2-alkoxycarbonyl derivatives of N-methylglucamine, unsaturated fatty acid monoglycerides, glycerol monooleate, glycerol monostearate, monolinolein, monoolein, $C_{12}EO_2$, $C_{12}EO_{23}$, and $C_{16}EO_3$, wherein EO represents an ethylene oxide group, and combinations thereof, which are capable of forming a cubic liquid crystalline phase;
   B) a polar solvent selected from the group consisting of water, glycerol, glycols, formamides, ethylammonium nitrate, and combinations thereof; and
   C) an additive selected from the group consisting of an ionic anchors and tethers, wherein the ionic anchors are selected from dioctyldecylamine hydrogen chloride, di(canola ethyl ester) dimethyl amine chloride, and potassium oleate and mixtures thereof, and the tether is selected from derivatized polysaccharides and linear substituted polymers and mixtures thereof;
   wherein (A), (B), and (C) are present in mass fractions relative to each other such that $$1.0 = a+b+c$$

wherein a is the mass fraction of (A), b is the mass fraction of (B), and c is the mass fraction of (C), and the mass-fractional relationship between a, b and c is $1.0 > a > 0$, $1.0 > b > 0$, $1.0 > c > 0$.

52. The precursor of claim 51 further comprising (D), an active ingredient selected from the group consisting of non-steroidal anti-inflammatory drugs, metronidazole, acetyl salicylic acid, clotrimazole, insulin, lidocaine hydrochloride, nitroglycerin, prilocaine, tetracycline hydrochloride, benzylpenicillin, acyclovir, guaifenesin, melatonin, metronidazole, phenylpropanolamine, pseudoephedrine hydrochloride, timolol maleate, acyclovir, hydrocortisone, minoxidil, sildenafil citrate, eflornithine HCl, zinc pyrithione, skin moisturizers, vitamins, minerals, and combinations thereof.

53. A cosmetic/pharmaceutical composition for topical application comprising a cubic liquid crystalline phase precursor consisting essentially of:
   (A) an amphiphile capable of forming a cubic liquid crystalline phase, wherein the amphiphile is a monoglyceride having the formula:

and R is selected from the group consisting of monovalent hydrocarbon groups of 6 to 22 carbon atoms, and monovalent halogenated hydrocarbon groups of 6 to 22 carbon atoms;
   (B) a polar solvent selected from the group consisting of water, glycerol, glycols, formamides, ethylammonium nitrate, and combinations thereof;
   (C) an additive selected from the group consisting of an ionic anchor, a tether, and combinations thereof; and
   (D) an active ingredient;

wherein (A), (B), and (C) are present in mass fractions relative to each other such that $$1.0 = a+b+c$$

wherein a is the mass fraction of (A), b is the mass fraction of (B), and c is the mass fraction of (C), and wherein the mass-fractional relationship between a, b and c is 1.0>a>0, 1.0>b>0, 1.0>c>0;

and with the proviso that a, b, and c do not fall within a cubic liquid crystalline phase region on a phase diagram representing phase behavior of (A), (B), and (C);

and wherein said active ingredient is selected from the group consisting of non-steroidal anti-inflammatory drugs, metronidazole, acetyl salicylic acid, clotrimazole, insulin, lidocaine hydrochloride, nitroglycerin, prilocaine, tetracycline hydrochloride, benzylpenicillin, acyclovir, guaifenesin, melatonin, metronidazole, phenylpropanolamine, pseudoephedrine hydrochloride, timolol maleate, acyclovir, hydrocortisone, minoxidil, sildenafil citrate, eflornithine HCl, zinc pyrithione, skin moisturizers, vitamins, minerals, and combinations thereof.

54. The cosmetic/pharmaceutical composition of claim 53, wherein (C) is an ionic anchor selected from the group consisting of positively charged surfactants and negatively charged surfactants.

55. The cosmetic/pharmaceutical composition of claim 54, wherein the anchor is a positively charged surfactant selected from the group consisting of quatemary surfactants, imidazoline based surfactants, substituted amino acids, and combinations thereof.

56. The cosmetic/pharmaceutical composition of claim 54, wherein the anchor is a negatively charged surfactant selected from the group consisting of alkyl carboxylates, modified carboxylates, isethionates, mono- and di-phosphate esters, alkyl sulphates, sulphonates, alkyl sulfonates, olefin sulfonates, alkyl benzene sulphonates, sulphosuccinates, and combinations thereof.

57. The cosmetic/pharmaceutical composition of claim 54, wherein (C) is a tether selected from the group consisting of derivatized polysaccharides, linear substituted polymers, star polymers, polypeptides, and polynucleotides, and combinations thereof.

58. The cosmetic/pharmaceutical composition of claim 57, wherein the tether is a derivatized polysaccharide selected from the group consisting of cellulose derivatives, chitin derivatives, starch derivatives, glycogen, glycoaminogylcans, lignan-based polymers, and combinations thereof.

59. The cosmetic/pharmaceutical composition of claim 57, wherein the tether is a linear substituted polymer selected from the group consisting of vinyl polymers, polyamines, polyamides, polyesters, polyphosphates, polysiloxanes polycarbonates, polyethoxylates, and combinations thereof.

60. The cosmetic/pharmaceutical composition of claim 57, wherein the tether is a polypeptide selected from the group consisting of polylysine, lipoproteins, and combinations thereof.

* * * * *

UNITED STATES PATENT AND TRADEMARK OFFICE
CERTIFICATE OF CORRECTION

PATENT NO. : 6,936,187 B2
DATED : August 30, 2005
INVENTOR(S) : Lynch et al.

It is certified that error appears in the above-identified patent and that said Letters Patent is hereby corrected as shown below:

Column 10,
Line 16, please change "pseudophedrine" to -- pseudoephedrine --.

Column 17,
Line 39, please change "positivcly charged" to -- positively charged --.
Line 46, please change "isetbionates" to -- isethionates --.

Column 19,
Line 29, please change "sisting of quatemary" to -- sisting of quarternary --.

Column 21,
Line 20, please change "sisting of quatemary" to -- sisting of quarternary --.

Column 25,
Line 30, please change "consisting of quatemary surfactants" to -- consisting of quarternary surfactants --.

Signed and Sealed this

Eighth Day of November, 2005

JON W. DUDAS
*Director of the United States Patent and Trademark Office*